(12) United States Patent
Russomano et al.

(10) Patent No.: US 8,454,534 B2
(45) Date of Patent: Jun. 4, 2013

(54) BLOOD COLLECTOR DEVICE AND BLOOD ANALYSIS PROCEDURE

(76) Inventors: Thais Russomano, Porto Alegre (BR);
Felipe Prehn Falcão, Porto Alegre (BR);
Mario Vian, Porto Alegre (BR);
Gustavo Dalmarco, Porto Alegre (BR);
Ricardo Bertoglio Cardoso, Porto Alegre (BR); Vishal Nangalia, Nuneaton (GB)

( * ) Notice: Subject to any disclaimer, the term of this patent is extended or adjusted under 35 U.S.C. 154(b) by 549 days.

(21) Appl. No.: 12/665,433

(22) PCT Filed: Jun. 18, 2007

(86) PCT No.: PCT/BR2007/000157
§ 371 (c)(1),
(2), (4) Date: Dec. 18, 2009

(87) PCT Pub. No.: WO2008/154710
PCT Pub. Date: Dec. 24, 2008

(65) Prior Publication Data
US 2010/0184118 A1    Jul. 22, 2010

(51) Int. Cl.
*A61B 10/02*  (2006.01)
*A61B 5/151*  (2006.01)
(52) U.S. Cl.
USPC ........... 600/583; 600/573; 606/181; 606/182; 606/183; 606/184; 606/185; 606/186
(58) Field of Classification Search
USPC ................ 600/573–584; 606/181–186, 188
See application file for complete search history.

(56) References Cited

U.S. PATENT DOCUMENTS

| | | | | |
|---|---|---|---|---|
| 4,690,153 A * | 9/1987 | Losada et al. | | 600/576 |
| 4,964,413 A * | 10/1990 | Losada et al. | | 600/579 |
| 5,871,494 A | 2/1999 | Simons et al. | | |
| 6,426,049 B1 * | 7/2002 | Rosen et al. | | 422/547 |
| 7,396,334 B2 * | 7/2008 | Kuhr et al. | | 600/583 |
| 7,854,896 B2 * | 12/2010 | Tyndorf et al. | | 422/547 |
| 2002/0141904 A1 * | 10/2002 | Rosen et al. | | 422/102 |
| 2002/0188223 A1 * | 12/2002 | Perez et al. | | 600/573 |
| 2003/0050573 A1 * | 3/2003 | Kuhr et al. | | 600/567 |
| 2003/0060730 A1 * | 3/2003 | Perez | | 600/576 |
| 2006/0030788 A1 * | 2/2006 | Wong et al. | | 600/583 |
| 2006/0155215 A1 * | 7/2006 | Cha et al. | | 600/583 |

FOREIGN PATENT DOCUMENTS
BR    P10203602    5/2004
BR    PI0203602.9 A *  5/2004

OTHER PUBLICATIONS

Russomano T. et al., A Device for Sampling Arterialized Earlobe Blood Austere Environments,. Aviation, Space, and Environmental Medicine, Apr. 2006, vol. 77, No. 4, pp. 453-455.*

* cited by examiner

*Primary Examiner* — Sean Dougherty
(74) *Attorney, Agent, or Firm* — Laurence P. Colton; Smith Risley Tempel Santos LLC

(57) ABSTRACT

The present invention provides an improved arterialized earlobe blood collection device, and an improved process for blood analysis. The device and the process of the invention can be used in many unsual and/or risky situations, including collecting arterialized blood in space missions under microgravity environment and within ambulances or the like. The process of the present invention enables easier and faster blood analysis, since the blood collector device of the invention is coupled with an analyzing apparatus so as no blood or needle manipulation is required.

20 Claims, 17 Drawing Sheets

BLOOD COLLECTOR DEVICE AND BLOOD ANALYSIS PROCEDURE

FIELD OF THE INVENTION

The present invention is related to a device and process to collect and analyze blood from the earlobe. More specifically, the present invention provides an improved device for blood collection which is advantageously used in space missions where microgravity avoids or poses huge challenges for blood collection with the currently available devices. The present invention also provides an improved process for blood analyses.

PRIOR ART

The increasing number and duration of space missions, followed by the flexibility of medical requirements for astronauts' selection, requires improvements over currently available astronaut's medical monitoring systems. This monitoring is made during Extra Vehicular Activities (EVA), in emergency situations or even during regular situations, and is usually performed by telemedicine thus requiring new techniques, procedures and devices adapted for microgravity environments.

Since blood has many functions within the body, many kinds of analyses can be performed so as to provide valuable information regarding the diagnosis of a number of medical conditions. Arterial gaseometry analyses, for example, are essential for the due clinic evaluation of astronauts since they provide essential physiologic information. Currently available devices and methods do not properly enable blood collection under microgravity conditions and also provoke contamination of the surrounding environment. Such devices and methods usually comprise puncturing and cannulation of an artery. Arterial cannulation or the positioning of an intra-arterial catheter is a technique which allows continuous and direct monitorization of blood pressure and also allows frequent sample withdrawal for blood analyses and gaseometry. By means of puncturing blood is usually collected from the wrist or from the inner part of the elbow or other artery. A needle is inserted in a previously cleaned area, generally also previously applying an anesthetic thereto. Blood flows into a syringe usually comprising heparin, and the needle is removed as soon as enough blood is collected. Both cannulation and puncturing are somehow painful and difficult techniques, and are indeed risky and prone to contaminating the environment, being therefore completely inadequate for microgravity conditions. On the other hand, studies show that capillary blood from the earlobe, when arterialized by means of massage, can be easily collected with a small cut. Studies also show that gaseometric data obtained with blood collected in such a way presents excellent correlation with that of the arterial blood.

Patent prior art comprises documents concerning blood collection devices. Although none of the found documents anticipates or suggests the present invention, neither alone nor in combination, the closest one is heretofore cited for reference.

Brazilian patent application BR 0203602-9, also of the present inventors, was the staring point for the development of the improved device and process of the present invention. Said document describes an arterialized earlobe blood collection device (ABCD) useful for space missions and therefore adapted for microgravity environments. The present invention provides an ABCD with a series of advantages over the device described in document BR 0203602-9, among which: reduced size, smaller weight, fewer parts and also the enabling of blood analyses such as gaseometric analyses within a single device.

One of the great technical advantages of the present invention lies in the conception of a device which, without contamination of the surrounding environment, enables the collection of arterialized blood from the earlobe for analyzing blood levels of oxygen and/or carbonic gas, pH, between other analyses. The present invention therefore overcomes several drawbacks in the art and is useful for a number of astronaut's medical evaluations, as well as for a number of terrestrial medical evaluations.

SUMMARY OF THE INVENTION

It is one of the objects of the invention to provide an improved arterialized earlobe blood collection device (ABCD). In one aspect, being therefore another object of the invention, the device of the present invention presents improvements on size, weight and mechanical parts.

It is another object of the invention to provide an improved process for collecting and analyzing blood. In one aspect, being therefore another object of the invention, the process of the present invention enables easier and faster blood analysis, since the blood collector device of the invention is coupled with an analyzing apparatus and no blood or needle manipulation is required.

These and other features of the invention will be better understood in the foregoing detailed description.

BRIEF DESCRIPTION OF THE FIGURES

FIGS. 1 to 5 show the blood collector devices described in document BR 0203602-9 (prior art), demonstrating the evolution of some blood collector devices.

FIG. 1 shows the first version of the prior art blood collector prototype, made of acrylic, polyacetal and inox.

FIG. 2 shows the second version of the prior art blood collector, made of acrylic, polyacetal and inox. It is smaller and lighter than the first one (FIG. 1). The cutting mechanism was improved also. On such version, the cutting mechanism was guided by a cam mechanism. When turning the back part of the collector, it releases the blade, which is pushed by a spring. After the cut, the blade is pushed back by the cam, and the capillary tube is placed to start collecting blood. Comparing to the previous version, such blood collector was improved, but it still heavy and difficult to handle.

FIG. 3 presents the third version of the prior art blood collector, made with aluminum and acrylic.

FIG. 4 shows the fourth version of the prior art blood collector, with a body made of aluminum and acrylic.

FIG. 5 shows the fifth version of the prior art blood collector, with body made of tecaform AH, back part of acrylic, and the blade cover of aluminum.

FIG. 6 displays the last version of the blood collector, which represents the present invention.

FIG. 8 compares the prior art blood collector device (as described in the Brazilian Patent Application BR 0203602-9, upper part) with the device of the present invention.

FIG. 9 compares the blade from the prior art blood collector device (as described in the Brazilian Patent Application BR 0203602-9, upper part) with the new blade used in the device of the present invention.

DETAILED DESCRIPTION OF THE INVENTION

Figure 1A:
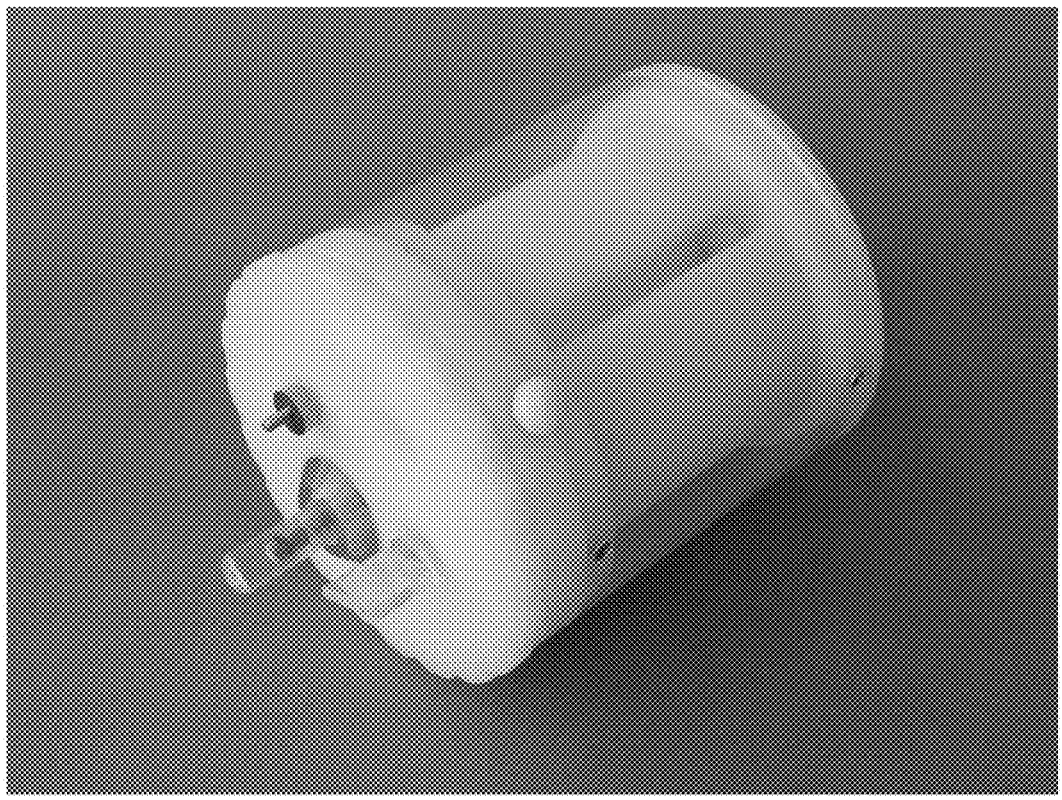
FIG. 1A is a first perspective view from a first end.
Figure 1B:
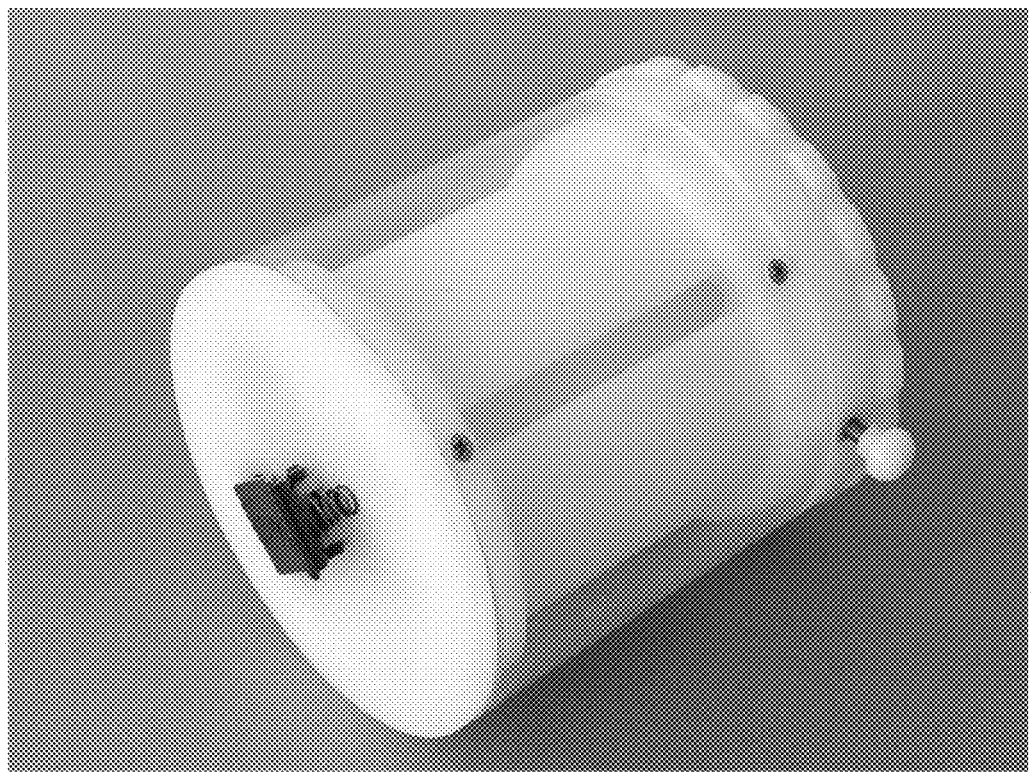
FIG. 1B is a second perspective view from a second end. The mechanism was activated by pushing the cutting device against the earlobe, exposing the blade and producing a 2.3 mm cut in the earlobe. Following this, it was necessary to release a lock, turning the back part of the collector to place the capillary tube in position, and initiating the blood collection. Such blood collector had some disadvantages like: heavy weight, big size, difficulty to see if the capillary tube is actually collecting blood and difficult handling. Besides that, the activation of the cutting mechanism depended on the strength of the user pushing it, rendering the obtention of a standardized cut very difficult.
Figure 2:
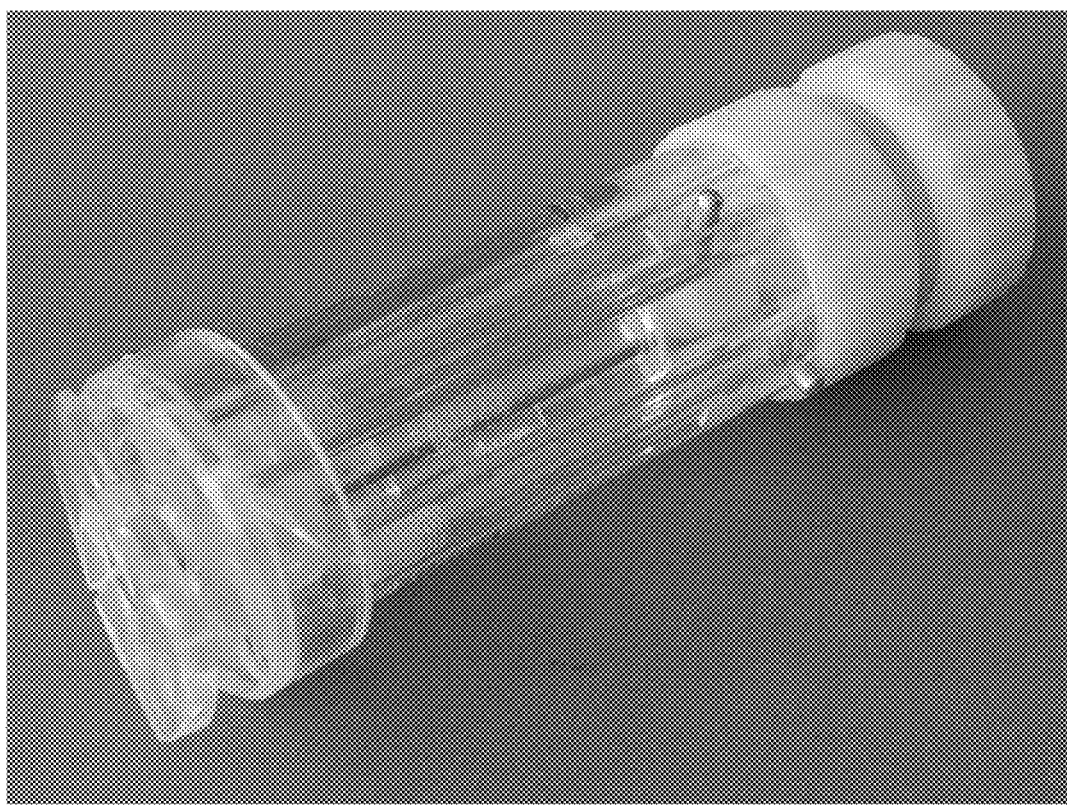
Figure 3A:
FIG. 3A is a perspective view and FIG. 3B is a side view. It is lighter and smaller than the two previous versions (FIGS. 1 and 2), and has the same cutting mechanism of the second blood collector. It was improved, but still difficult to handle and to change the blade and capillary tube.
Figure 3B:
Figure 4A:
FIG. 4A is a side view and FIG. 4B is a perspective view. It has the same cam mechanism, but with a new blade. It is lighter and smaller than the previous versions, but still not satisfactory. It has a different grip system, that covers the cam mechanism and increases the holding area, making it easier to handle.
Figure 4B:
Figure 5A:
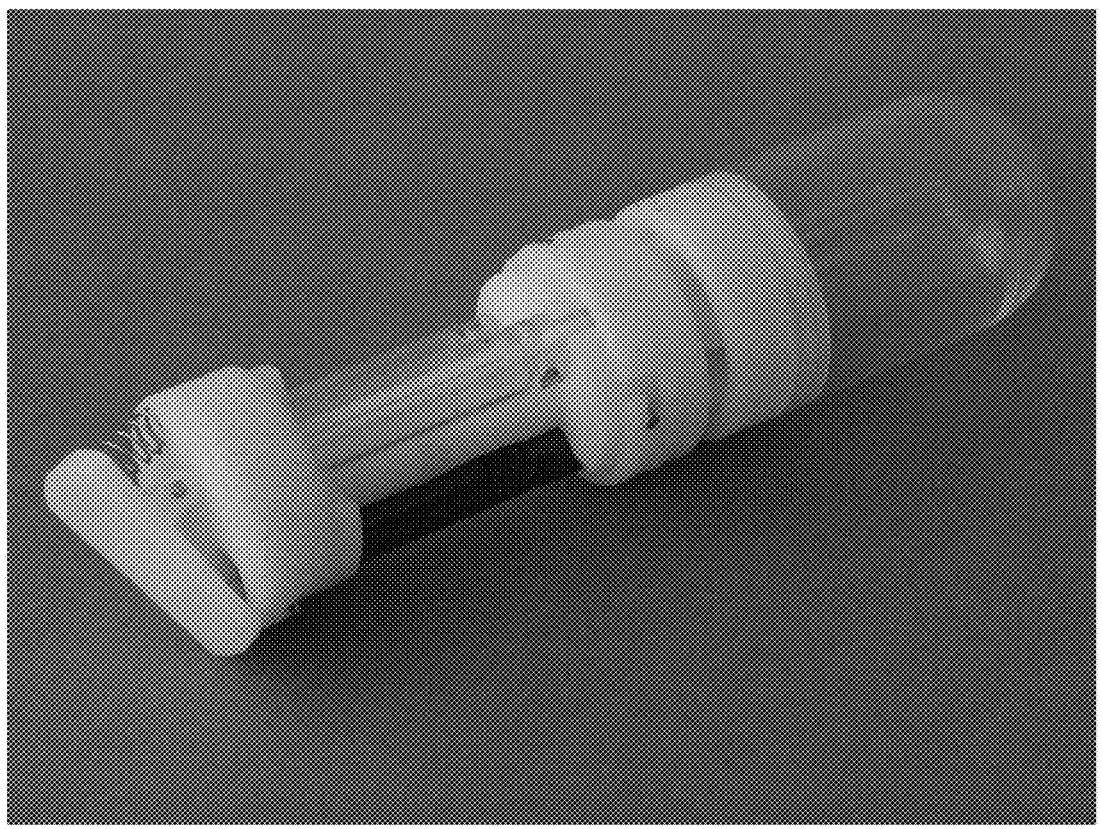
FIG. 5A is a first perspective view from a first end.
Figure 5B:
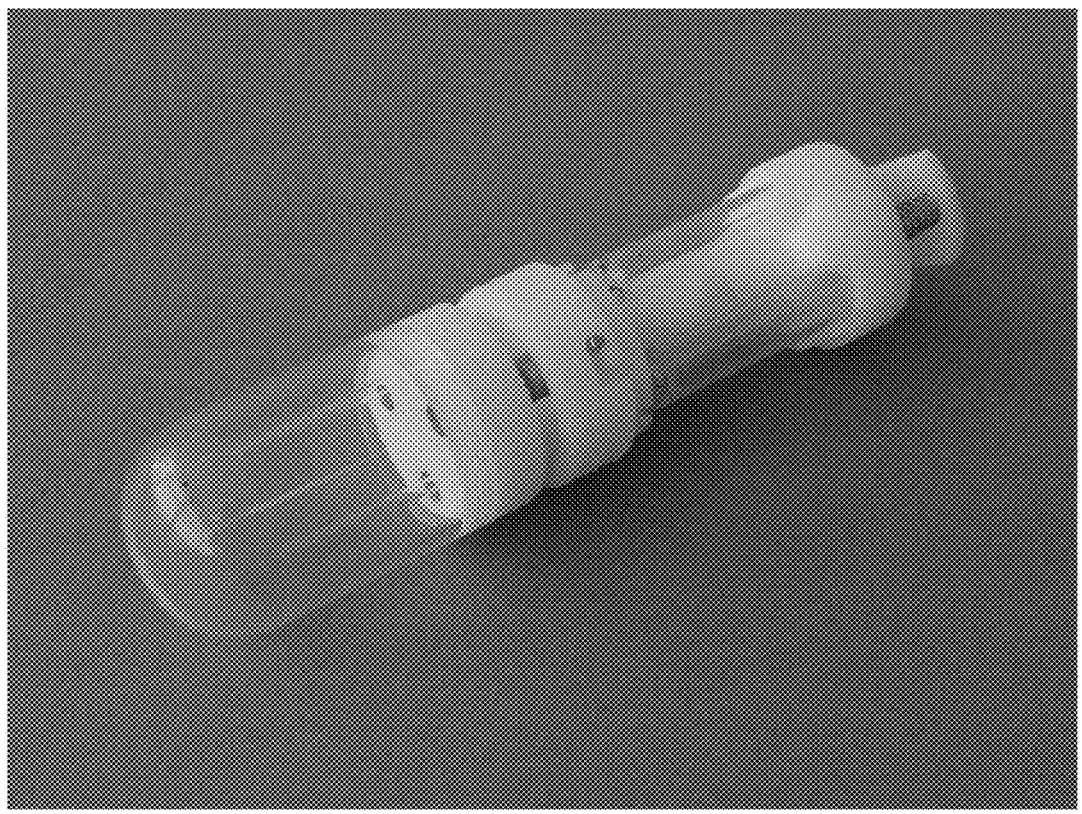
FIG. 5B is a second perspective view from a second end. Such a version has all the improvements that were needed on the previous versions, but it still does not allow the user to analyze the blood. To do this, it is necessary to unscrew the back part, remove the capillary tube and connect it with a blood analysis machine.
Figure 6A:
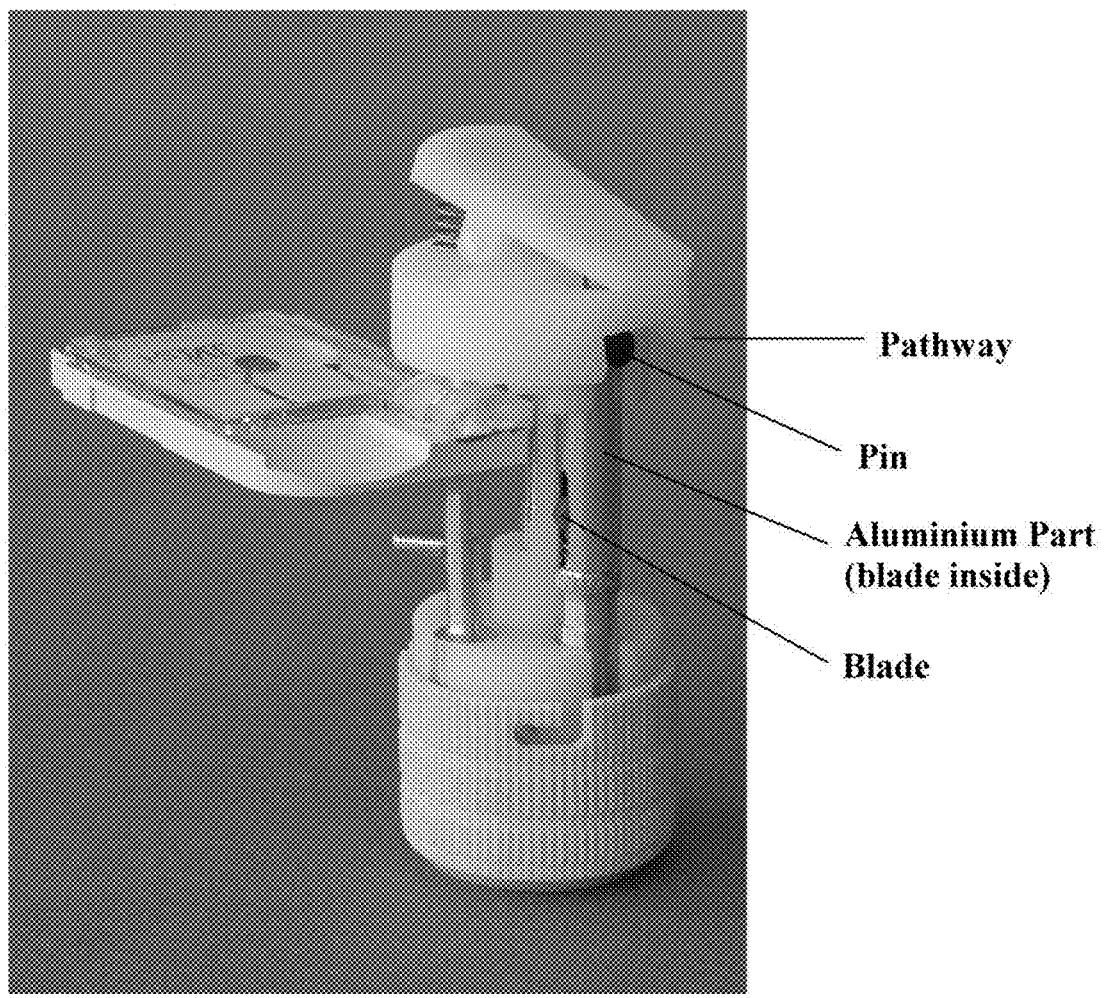
FIG. 6A is a side view of the constructed device and FIG. 6B is a view of the deconstructed device. Compared to the previous versions of blood collectors, it is smaller and lighter. It also has fewer mechanical parts and enables the blood collection and analysis in the same device, by simply connecting the cartridge adapted to it in a portable blood analyzing machine.
Figure 6B:
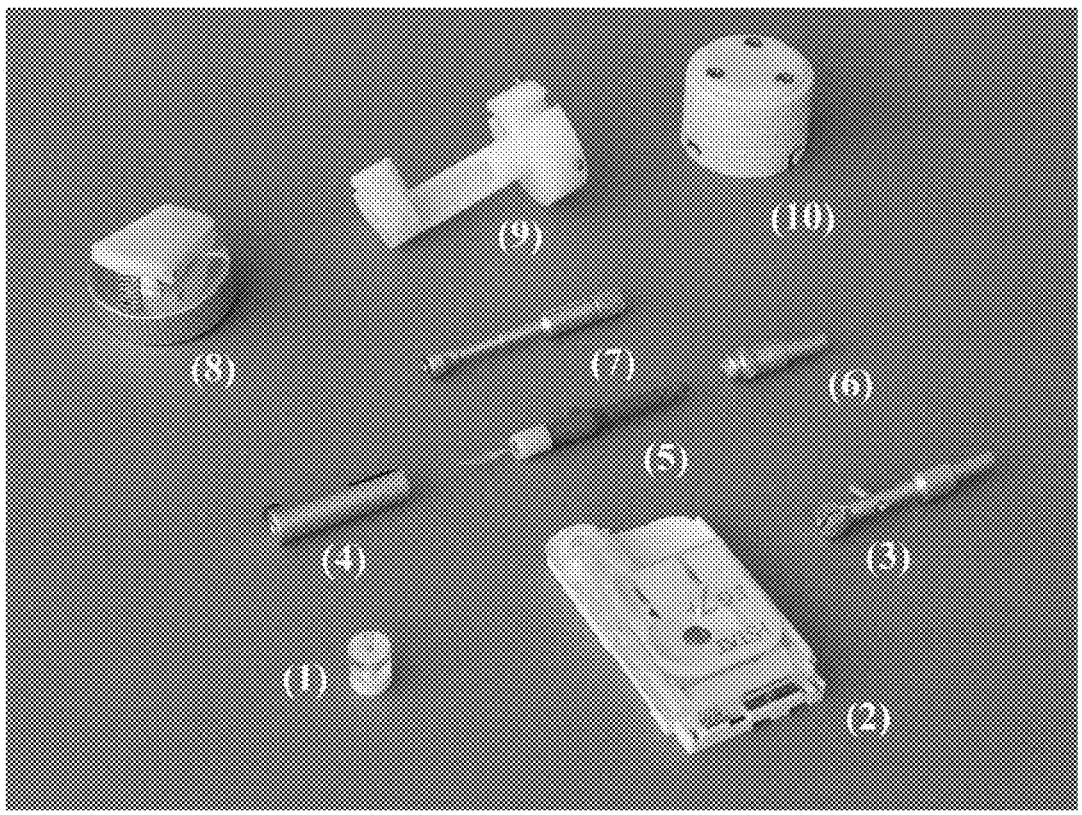
Figure 7:
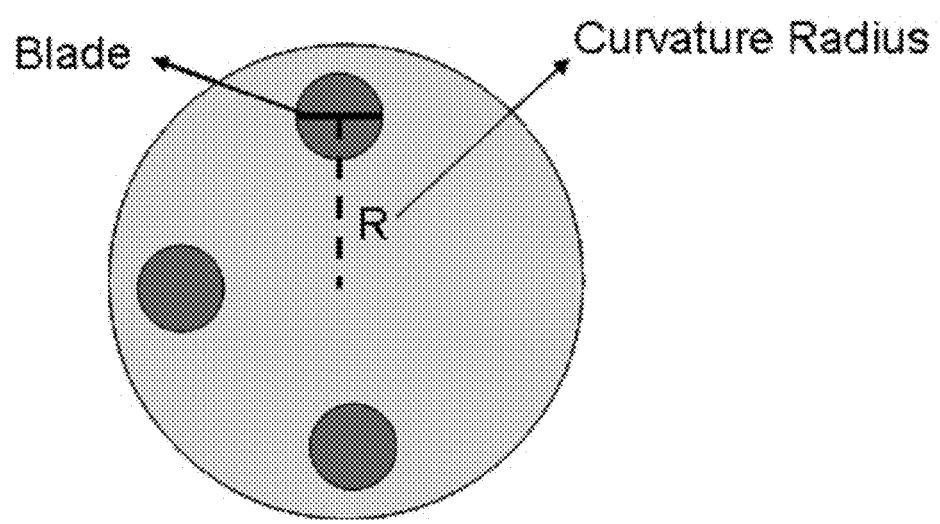
FIG. 7 illustrates a transversal cut of the blood collector device of the present invention, indicating the curvature radius and three holes (one for the blade and other two for capillary tubes or cartridge).
Figure 8A:
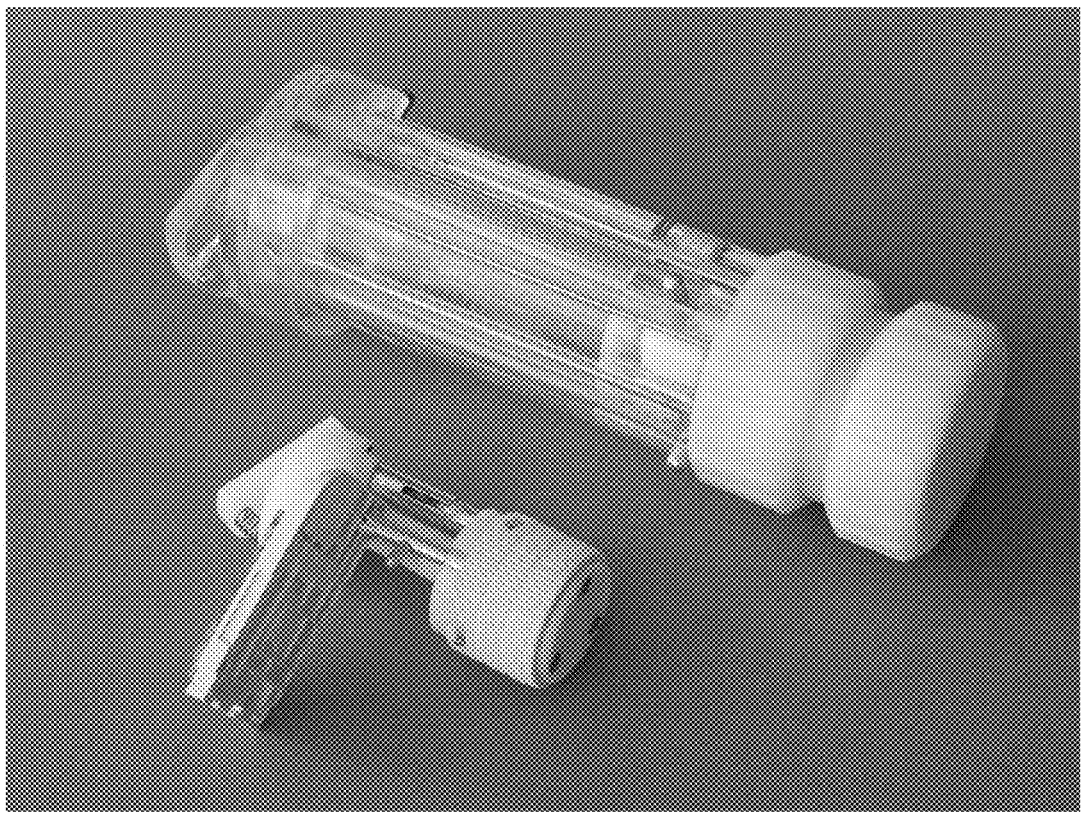
FIG. 8A comprises perspective views from a first side of the prior art device (the top device) and of the present invention (the bottom device).
Figure 8B:
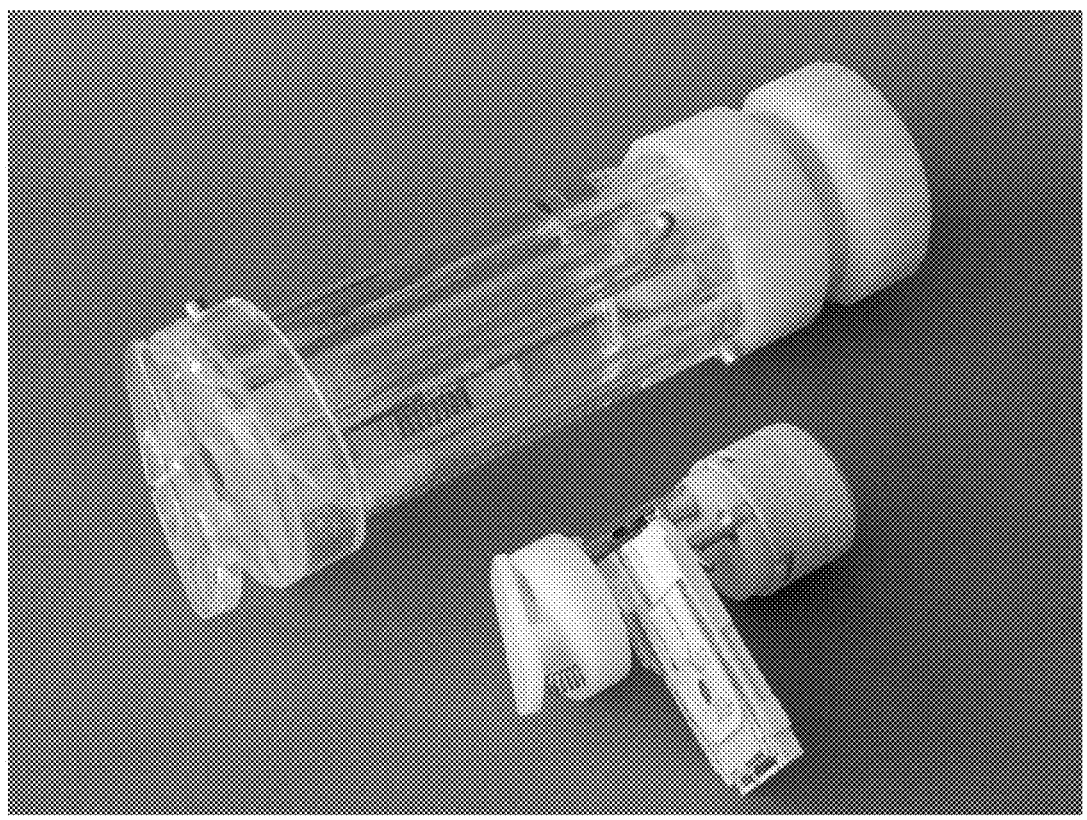
FIG. 8B comprises perspective views from a second side of the prior art device (the top device) and of the present invention (the bottom device).
Figure 9A:
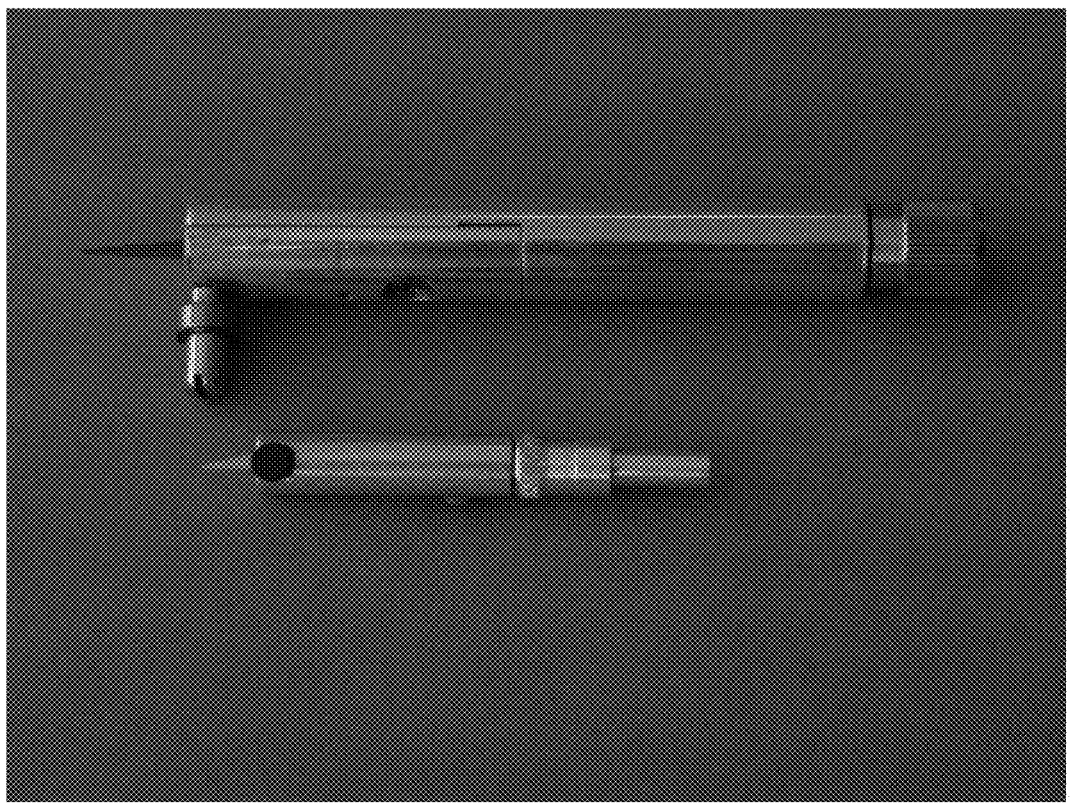
FIG. 9A comprises side views of the prior art device blade (the top device) and of the present invention (the bottom device).
Figure 9B:
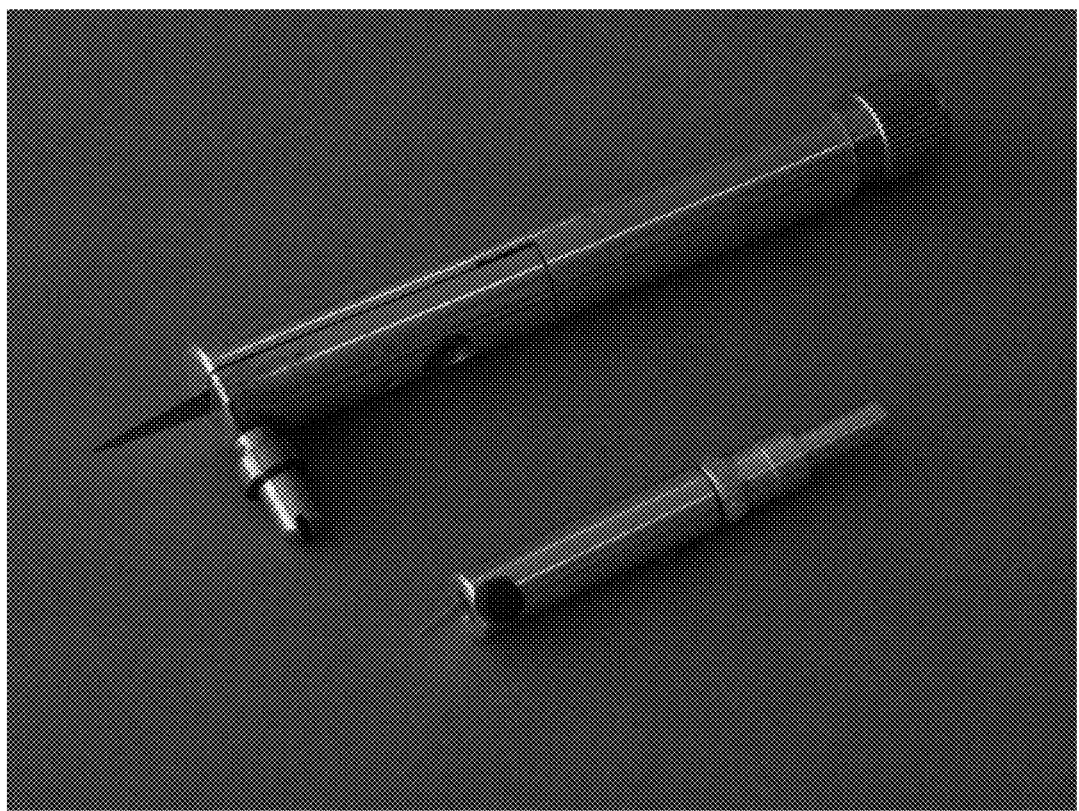
FIG. 9B comprises perspective views of the prior art device blade (the top device) and of the present invention (the bottom device).
Figure 10:
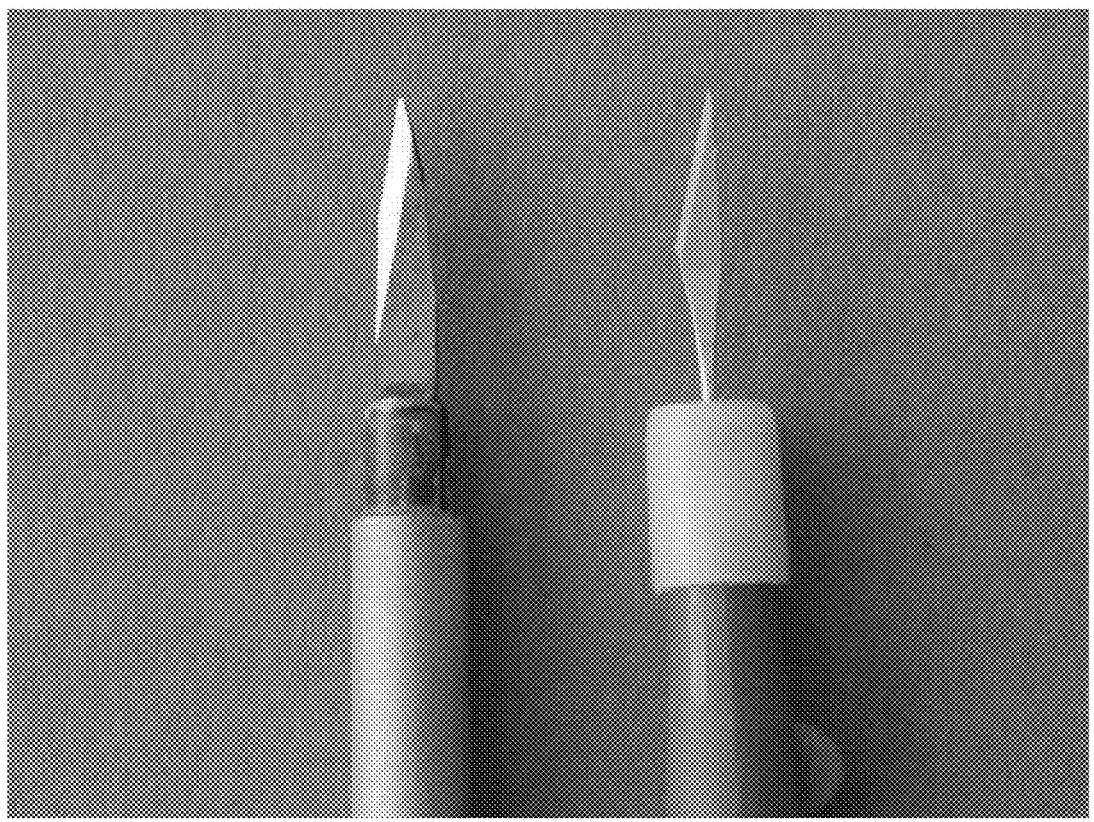
FIG. 10 shows in more detail the blade of the prior art blood collector device (as described in the Brazilian Patent Application BR 0203602-9, right) and the new blade used in the device of the present invention (left).

The present invention enables advantageous blood collection from the patient's earlobe. This technique is suitable for use in microgravity environments and can therefore be used to perform blood collection in space missions.

The arterialized earlobe blood collector of the invention comprises a fixation and sealing part, working both as an interface of the blood collector and the human anatomy, to prevent blood leaking, and as a support structure to a collection device that is used to collect and store the blood. The fixation and sealing device avoids contamination of the environment, and acts as a second barrier against any blood leakage.

The arterialized blood collector device of the invention comprises two modules (cut and blood collection). The front part of the device has an opening that aligns the modules with the earlobe. By turning the back part with one hand, and holding the front part with the other hand, the modules are activated in sequence (first cut then collect). To collect the blood, it is necessary to attach the device to the arterialized earlobe, holding the front part with one hand, and turning the back part with the other hand. By turning the device, the blade is exteriorized, guided by a cam mechanism. As a continuous movement, the blade cuts the earlobe and retracts exteriorizing then the collecting module. After the collection, the device is removed from the earlobe, and connected to the analyzing device.

The cutting module consists of an aluminum body, where the blade is adapted to work with the blood collector. The aluminum body has a plastic pin, in the front end (above the blade), that is used as a guide for the cam system. To close the aluminum body, there is a cap in the back end, which is screwed to the front part. This screwing system allows adjusting the blade also, regulating the depth of cut. It is pushed against the earlobe by the action of a spring.

The arterialized blood collector of the present invention has several improvements over the previous versions, including improvements on the blood collector device body, and on the cutting and collecting modules. On the device body, the back cap was adapted to comprise a quick fastener system. This way, it is now easier to open and to close the device, allowing quick change of the modules and maintenance. With four pins connected to the body of the device, and four L-shaped entrances on the cap, it provides a quick and sharp closing of the device, avoiding leakage or any possibility of undesired opening during use. In the previous version, the closing system was made by screwing the cap in the body of the device, which was very difficult to handle when wearing procedure gloves.

Several changes were made on the cutting module also. The main one was the change of the blade, for a blade used in ophthalmic surgery. This change was necessary due to the need of lathing the old blade and sterilizing it to adapt to the blood collector. With this new blade, it is possible to take it from the package and place it straight in the cutting module, without needing to lathe.

The new collecting module also has a new closing mechanism, which consists of a cap which is screwed to the front part of the module. By screwing the cap, it is possible to adjust the length of the exposed part of the blade, then adjusting the depth of the cut. In addition to that, the new blade is thinner (0.15 mm, while the old blade has 0.4 mm), providing a better flow of blood from the cut.

Another modification was made in the cutting module. The guiding pin was changed from a bearing pin to a plastic one. As the body of the blood collector was changed to tecaform AH, the plastic pin had less superficial resistance than the one with bearing. These changes resulted in less mechanical parts in the cutting module, decreasing the necessity of maintenance.

Another important change was made in the collecting module. In the previous version, after collecting the blood, it was necessary to unscrew the back cap, remove the capillary tube and place it into the equipment that could analyze the blood. This procedure was difficult to be performed, due to the size and complexity of operation of the analyzing equipment, and the difficulty to unscrew the back part of the collector wearing procedure gloves. In the present invention, after cutting the ear and positioning the collection module, it is possible to visualize the cartridge filling with blood, due to the presence of a small window now introduced in the device of the invention. Following the blood collection, it is only necessary to rotate the cartridge less than 90°, and connect it to a portable analyzing equipment such as that known as Abbott I-Stat.

After connecting it, it is only necessary to click one button, and the result is ready in about 2 min. For enabling the collection and analysis of blood within a single piece of equipment, and getting the results in 2 min, the device of the invention is useful is a series of situations not limited to microgravity conditions, such as use in ambulances, health care units and even at home.

Furthermore, the blood collector device of the invention is both portable and disposable. In summary, the blood collector device of the invention has a series of improvements over the blood collector described in the Brazilian Patent Application BR 0203602-9, of the same inventors. These changes and improvements include:

(i) the change of blade number 11 to another one used in ophthalmological surgeries (Manufacturer: Sharpoint; Model: Stab Knife Straight 15°; Ref: 72-1502). This change was made in view of the following considerations: (1) to reduce the discomfort as a consequence of the cut; (2) as the new blade is thinner (0.15 mm thick, while blade number 11 has 0.4 mm), the blood flow provided from the cut is enhanced; (3) with the new blade, it is not necessary to lathe and sterilize the blade in order to adapt it to the ABCD, because the new blade can be connected directly in the cutting module. With the old blade, it was necessary to lathe and sterilize it. The new version can use the blade directly after removal from the package;

(ii) changing the blade, the cutting module was adapted to the new blade and also to the new material of the blood collector device body. As it was changed to tecaform AH, the plastic pin has less superficial resistance than the one with bearing. These changes resulted in less mechanical parts in the cutting module, reducing the necessity of maintenance;

(iii) a screwing system was adapted in the cutting module, so as to both close the module and adjust the length of the exposed part of the blade. This way, it is now possible to extend or retract the blade, adjusting the depth of the cut;

(iv) the blood collection module was changed, replacing the capillary tube with a cartridge for blood analysis. The preferred cartridge for the invention is that manufactured by Abbott (I-Stat), which allows many blood analyses according to the cartridge model;

(v) introducing a window so as to see the blood while it is filling the cartridge. With this window, it is now possible to see when the cartridge is full of blood so as to stop the collection;

(vi) on the device body, the back cap was adapted to comprise a quick fastener system. It is now therefore easier to open and close the device, allowing quick change of the modules and maintenance. With four pins connected to the body of the device, and four "L" entrances on the cap, it provides a quick and sharp closing of the device, avoiding leakage or any possibility of undesired opening during use. In the previous version, the closing system was made by screwing the cap in the body of the device, which was very difficult to handle, mainly when wearing procedure gloves;

(vii) by adding the cartridge, reducing both size and weight and improving the handling, it is now possible to perform in loco blood collection and analysis, preferably using the Abbott (I-Stat) blood analyzer. After collecting the blood, the ABCD is connected to the blood analyzing device, which analyzes the blood and shows the results in few minutes.

On the previous version described in the Brazilian Patent Application BR 0203602-9 it was necessary to disassemble the device in order to remove the collecting module with blood, and put it into the gaseometric blood analysing equipment. Due to the size and complexity to assemble and handle the ABCD, it was difficult to perform this procedure. With the device of the present invention, the only thing to do is to turn the cartridge and connect it to the portable blood analyzer equipment, such as that of Abbott. After that, it is just necessary to click one button and wait 2 minutes for the results. Table 1 compares technical features of the ABCD of the prior art and those of the device of the present invention.

TABLE 1

| ABC's Technical Features | |
|---|---|
| ABC of BR 0203602-9 | ABC of the present invention |
| Length = 138 mm | Length = 57 mm |
| Diameter = 40 mm | Diameter = 26 mm (55 mm with cartridge) |
| Weight = 228 g | Weight = 23.58 g (29.50 g with cartridge) |
| Blade: Blade 11 | Blade: Stab Knife Straight 15° |
| Material: Acrylic, Polyacetal & Inox | Material: Tecaform AH, Acrylic & Aluminium |
| Structure: 4 stages (Cut, 2 Collect, Gauze) | Structure: 2 stages (Cut, Collect) |
| Cut: Length: 3 mm | Cut: Length: 4.5 mm |
| Depth: 1.7 mm | Depth: 3 mm |
| Curvature Radius: 12 mm | Curvature Radius: 8 mm |

Even though it was developed with the main purpose of collecting blood in microgravity conditions, the present invention can also be used in regular gravity. Since it enables the collection of arterialized blood from the earlobe, the ABCD of the invention is also an ideal means for use in substitution to arterial puncturing, which is much more painful and risky. The ABCD of the invention can therefore be used in hospitals, ambulances and health care units, permitting the realization of exams that are usually not made outside hospitals and/or laboratories. The skilled person will readily appreciate the teachings of the present invention. Subtle variations in the device and/or herein described should be deemed as within the scope of the invention and of the appended claims.

The invention claimed is:

1. An arterialized earlobe blood collector device comprising:
 a blood collecting module comprising at least one cartridge for blood collecting;
 a cutting module comprising an ophthalmic surgery blade in an aluminum body and at least one screwing system having a blade depth adjusting means; and
 a device body comprising a back part having a quick fastener mechanism for opening and closing the device, an anatomic ear attachment system, and a sealing system.

2. The device according to claim 1, wherein said quick fastener mechanism comprises four pins attached to the back part of the device, and a cap comprising four L-shaped depressions, wherein each of the pins are connected to a respective one of the L-shaped depressions for closing.

3. The device according to claim 2, wherein said blade has a thickness between 0.1 mm and 0.4 mm.

4. The device according to claim 3, wherein said blade has a thickness of 0.15 mm.

5. The device according to claim 3, wherein the blade is spring-pushed, and further comprising a plastic pin which releases the spring-pushed blade via a cam mechanism.

6. The device according to claim 3, further comprising a window enabling visualization of blood during collection of blood.

7. The device according to claim 2, wherein the blade is spring-pushed, and further comprising a plastic pin which releases the spring-pushed blade via a cam mechanism.

8. The device according to claim 7, further comprising a window enabling visualization of blood during collection of blood.

9. The device according to claim 2, further comprising a window enabling visualization of blood during collection of blood.

10. The device according to claim 1, wherein the blade has a thickness between 0.1 mm and 0.4 mm.

11. The device according to claim 10, wherein said blade has a thickness of 0.15 mm.

12. The device according to claim 10, wherein the blade is spring-pushed, and further comprising a plastic pin which releases the spring-pushed blade via a cam mechanism.

13. The device according to claim 10, further comprising a window enabling visualization of blood during collection of blood.

14. The device according to claim 1, wherein the blade is spring-pushed, and further comprising a plastic pin that releases the spring-pushed blade via a cam mechanism.

15. The device according to claim 14, further comprising a window enabling visualization of blood during collection of blood.

16. The device according to claim 1, further comprising a window enabling visualization of blood during collection of blood.

17. A blood analysis process wherein arterialized blood is collected by means of a device comprising:
attaching the device to an earlobe via a means for attaching the device to an earlobe;
sealing the device to an earlobe via a means for sealing the device to an earlobe, wherein the sealing device avoids leakage of blood between the device and an earlobe;
collecting blood via a means for collecting blood, said means for collecting blood comprising at least one cartridge and a screw system having a blade depth adjusting means; and
avoiding blood manipulation and conducting blood analysis in vitro once collected blood is located on the at least one cartridge that is directly associated to an analysis device,
wherein the device comprises a back part and a means for quick fastening of the back part of the device.

18. The blood analysis process according to claim 17, further comprising a blade and using said blade to cut the earlobe, wherein cut depth of the blade is adjustable by means of retraction or extension of an exposed part of the blade.

19. The blood analysis process according to claim 18, further comprising, after collecting blood, coupling the at least one cartridge to an analyzer to avoid blood manipulation.

20. The blood analysis process according to claim 17, further comprising, after collecting blood, coupling the at least one cartridge to an analyzer to avoid blood manipulation.

* * * * *